(12) United States Patent
Tsay et al.

(10) Patent No.: US 6,815,653 B2
(45) Date of Patent: Nov. 9, 2004

(54) METHOD AND APPARATUS FOR EARLY DETECTION OF MATERIAL ACCRETION AND PEELING IN PLASMA SYSTEM

(75) Inventors: Jenq-Yann Tsay, Tainan (TW); Jeng-Chiang Chuang, Kaohsiung (TW); Chih-Pen Yen, Kaohsiung (TW); Yung-Mao Hsu, Tainan (TW)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 73 days.

(21) Appl. No.: 10/122,687

(22) Filed: Apr. 15, 2002

(65) Prior Publication Data

US 2003/0193010 A1 Oct. 16, 2003

(51) Int. Cl.$^7$ ............................................. H01L 21/306
(52) U.S. Cl. .................. 250/206; 250/574; 156/345.34; 216/60; 118/715; 134/1.1
(58) Field of Search ................................. 250/206, 221, 250/573, 574; 156/345.33–345.35; 216/58–60; 438/706, 710; 118/715, 716; 134/1.1, 1.2

(56) References Cited

U.S. PATENT DOCUMENTS

| 5,637,881 | A | * | 6/1997 | Burghard et al. ............ 250/573 |
| 6,117,348 | A | * | 9/2000 | Peng et al. .................... 216/60 |
| 2003/0038112 | A1 | * | 2/2003 | Liu et al. ...................... 216/60 |

* cited by examiner

Primary Examiner—Thanh X. Luu
Assistant Examiner—Stephen Yam
(74) Attorney, Agent, or Firm—Tung & Associates

(57) ABSTRACT

A method and apparatus for detecting material accretion and peeling in a system such as a plasma process chamber, including multiple optical sensors which are provided in the chamber above a gas distribution plate or other surface inside the chamber. The optical sensors are connected to a central process controller that is capable of terminating operation of the chamber and may be equipped with an alarm. In the event that the optical sensors detect asymmetries in brightness or light reflection among various portions or regions of the gas distribution plate or other surface, which asymmetries may indicate the formation of a material coating on the plate or dislodging of contaminant particles from the plate, a signal is sent to the process controller, which may be adapted to terminate the plasma process, alert operating personnel, or both.

14 Claims, 2 Drawing Sheets

US 6,815,653 B2

METHOD AND APPARATUS FOR EARLY DETECTION OF MATERIAL ACCRETION AND PEELING IN PLASMA SYSTEM

FIELD OF THE INVENTION

The present invention generally relates to fabrication of semiconductor integrated circuits and more particularly, to an apparatus and method for detecting material accretion and dislodging from a quartz gas distribution plate (GDP) in a plasma process chamber during semiconductor wafer processing.

BACKGROUND OF THE INVENTION

In the semiconductor production industry, various processing steps are used to fabricate integrated circuits on a semiconductor wafer. These steps include the deposition of layers of different materials including metallization layers, passivation layers and insulation layers on the wafer substrate, as well as photoresist stripping and sidewall passivation polymer layer removal. In modern memory devices, for example, multiple layers of metal conductors are required for providing a multi-layer metal interconnection structure in defining a circuit on the wafer. Chemical vapor deposition (CVD) processes are widely used to form layers of materials on a semiconductor wafer.

CVD processes include thermal deposition processes, in which a gas is reacted with the heated surface of a semiconductor wafer substrate, as well as plasma-enhanced CVD processes, in which a gas is subjected to electromagnetic energy in order to transform the gas into a more reactive plasma. Forming a plasma can lower the temperature required to deposit a layer on the wafer substrate, to increase the rate of layer deposition, or both. However, in plasma process chambers used to carry out these various CVD processes, materials such as polymers are coated onto the chamber walls and other interior chamber components and surfaces during the processes. These polymer coatings frequently generate particles which inadvertently become dislodged from the surfaces and contaminate the wafers.

In semiconductor production, the quality of the integrated circuits on the semiconductor wafer is directly correlated with the purity of the fabricating processes, which in turn depends upon the cleanliness of the manufacturing environment. Furthermore, technological advances in recent years in the increasing miniaturization of semiconductor circuits necessitate correspondingly stringent control of impurities and contaminants in the plasma process chamber. When the circuits on a wafer are submicron in size, the smallest quantity of contaminants can significantly reduce the yield of the wafers. For instance, the presence of particles during deposition or etching of thin films can cause voids, dislocations, or short-circuits which adversely affect performance and reliability of the devices constructed with the circuits.

Particle and film contamination has been significantly reduced in the semiconductor industry by improving the quality of clean rooms, by using automated equipment designed to handle semiconductor substrates, and by improving techniques used to clean the substrate surfaces. However, as deposit of material on the interior surfaces of the processing chamber remains a problem, various techniques for in-situ cleaning of process chambers have been developed in recent years. Cleaning gases such as nitrogen trifluoride, chlorine trifluoride, hexafluoroethane, sulfur hexafluoride and carbon tetrafluoride and mixtures thereof have been used in various cleaning applications. These gases are introduced into a process chamber at a predetermined temperature and pressure for a desirable length of time to clean the surfaces inside a process chamber. However, these cleaning techniques are not always effective in cleaning or dislodging all the film and particle contaminants coated on the chamber walls. The smallest quantity of contaminants remaining in the chamber after such cleaning processes can cause significant problems in subsequent manufacturing cycles.

SUMMARY OF THE INVENTION

Therefore, it is an object of the present invention to detect the presence of material accretion on interior components of a plasma process chamber during the processing of semiconductors.

A further object of the present invention is to detect the dislodging of potential contaminant particles from an interior surface of a plasma process chamber during the processing of semiconductors.

Still another object of the present invention is to provide for continuous monitoring of a plasma process chamber during the processing and fabrication of semiconductor integrated circuits in order to prevent or minimize particle contamination of one or multiple semiconductor wafers.

Yet another object of the present invention is to provide a mechanism which utilizes differences in brightness, opacity or reflective index of a surface inside a plasma process chamber to reveal material accretion on and/or particle dislodging from the surface for potential wafer substrate contamination.

A still further object of the present invention is to prevent or reduce contamination of a semiconductor wafer substrate inside a plasma process chamber by utilizing multiple light sensors which detect differences in brightness or reflective index of a gas distribution plate (GDP) inside the chamber to monitor material accretion on and/or dislodging of potential contaminating particles from the plate.

In accordance with these and other objects and advantages, the present invention comprises multiple optical sensors which are provided in the top portion of a plasma process chamber above a gas distribution plate of the chamber and are connected to a central process controller that is capable of terminating operation of the chamber and may be equipped with an alarm. In the event that the optical sensors detect relative disparities or asymmetries in brightness or light reflective index among various portions or regions of the gas distribution plate, which disparities or asymmetries may indicate the formation of a material accretion or coating on the plate or dislodging of contaminant particles from the plate, a signal is sent to the process controller, which may be adapted to terminate the plasma process, alert operating personnel, or both.

BRIEF DESCRIPTION OF THE DRAWINGS

The present invention will now be described, by way of example, with reference to the accompanying drawings, in which.

DESCRIPTION OF THE PREFERRED EMBODIMENTS

When used herein, the term optical sensor shall be understood to mean any device which is capable of detecting light radiation or reflection from a surface. When used herein, the term process controller shall be understood to mean any device capable of calculating light reflective indices and determining differences in light radiation or light reflective indices responsive to differential data input from multiple optical sensors, and/or comparing light radiation or reflective index data input with a standard value and modulating the operation of a system accordingly. When used herein, the term alarm shall be understood to mean any device capable of indicating a condition by audio alarm, video alarm, or both, responsive to data input.

The present invention has particularly beneficial utility in application to monitoring polymer or other material coating, accretion or buildup on a gas distribution plate (GDP) in a plasma process chamber. However, the invention is not so limited in application, and while references may be made to such gas distribution plate and plasma process chamber, the invention may be more generally applicable to detecting coating buildup and/or fragmentation and dislodgment on other interior surfaces of a plasma process chamber or other closed system.

Figure 1:
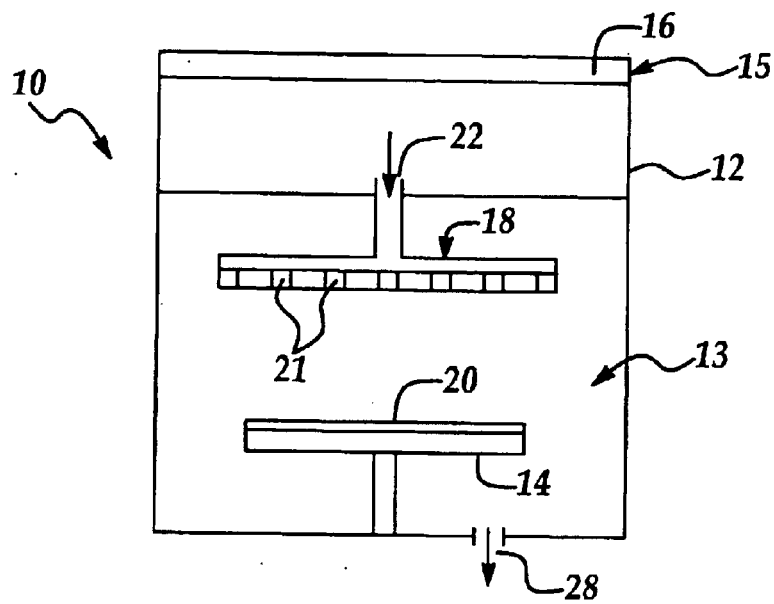
FIG. 1 illustrates interior components of a conventional plasma process chamber.

A conventional plasma process chamber is generally indicated schematically by reference numeral 10 in FIG. 1. The plasma process chamber 10, also known in the art as a plasma etch reactor, includes a housing 12 which is typically constructed of a nonmagnetic material such as aluminum and defines a chamber interior 13. A clamp lid assembly 15 including a lid 16 is removably attached to the housing 12 for selectively sealing the chamber interior 13. A wafer platform 14 is provided in the bottom portion of the chamber interior 13 for supporting a semiconductor wafer 20, which wafer platform 14 further acts as a cathode. A quartz gas inlet nozzle 18, or "showerhead", also known in the art as a gas distribution plate (GDP), is mounted in the chamber interior 13, directly above the wafer platform 14. Reaction gases introduced through a gas inlet 22 flow into the chamber interior 13 through multiple openings 21 in the gas distribution plate 18.

During operation of the conventional plasma process chamber 10, the semiconductor wafer 20 is heated in the chamber interior 13 and is selectively cooled by a cooling gas (not illustrated) as the wafer 20 transfers heat to the water-cooled wafer platform 14. Precursor reaction gases flowing into the chamber interior 13 through the openings 21 in the gas distribution plate 18 are typically reacted with the heated substrate semiconductor wafer 20. Alternatively, the reaction gases may be subjected to electromagnetic energy to form a reactive plasma which is capable of reacting with the semiconductor wafer 20 at lower temperatures. As the gases or plasma reacts with the wafer 20, various films or layers such as metallization layers, passivation layers, insulation layers, etc., depending upon the chemical composition of the reaction gases or plasma, are deposited on the wafer 20 for the fabrication of integrated circuits on the wafer 20. An exhaust gas outlet 28, which is normally connected to a vacuum pump (not illustrated), is used to evacuate the gases or plasma from the chamber interior 13.

One of the problems inherent in such chemical vapor or plasma deposition processes is that layer or film deposition is not limited to the wafer 20, but polymer or other material coatings may be deposited on other surfaces in the chamber interior 13. Particularly problematic in this regard is the accretion of films or coatings on the gas distribution plate 18, which films or coatings are a significant source of particulate contaminants that frequently become dislodged from the gas distribution plate 18 as a result of mechanical and thermal stresses. The dislodged particulate contaminants tend to fall from the gas distribution plate 18 and contaminate the underlying wafer 20, and these impurities significantly compromise the functional integrity of the integrated circuits formed on the wafer 20.

Figure 2:
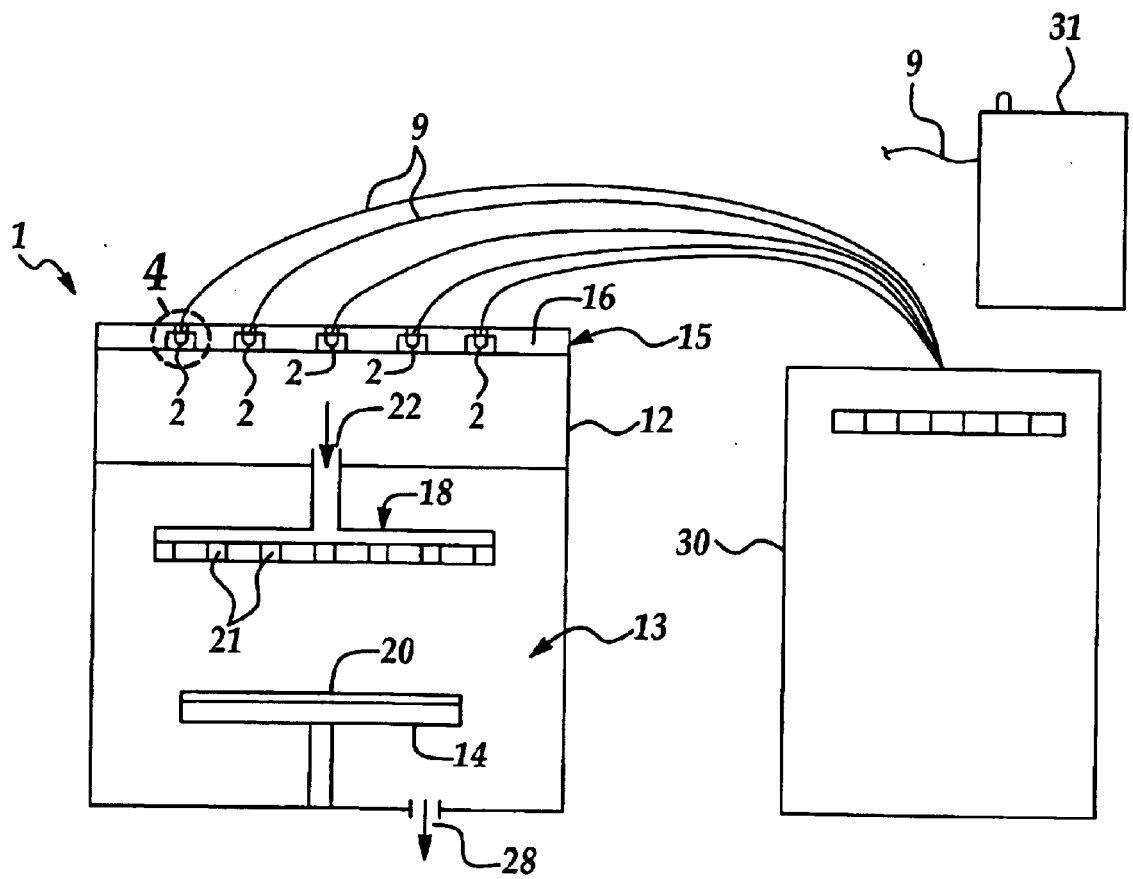
FIG. 2 illustrates a plasma process chamber according to the present invention, which plasma process chamber is provided with an apparatus for early detection of material accretion and peeling.
Figure 3:
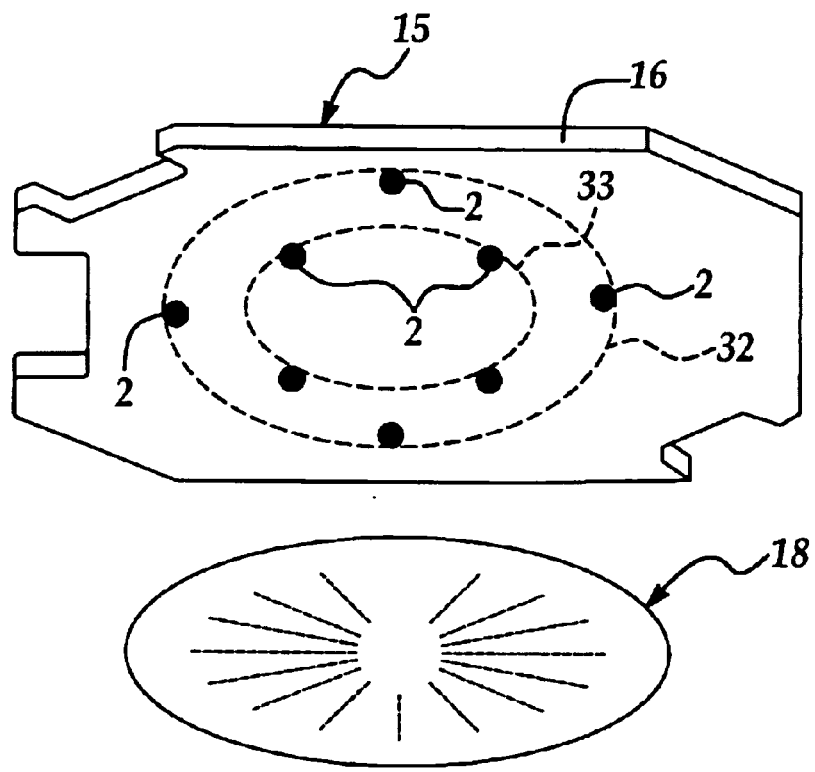
FIG. 3 is a bottom perspective view of the lid and gas distribution plate components of the plasma process chamber illustrated in FIG. 2.
Figure 4:
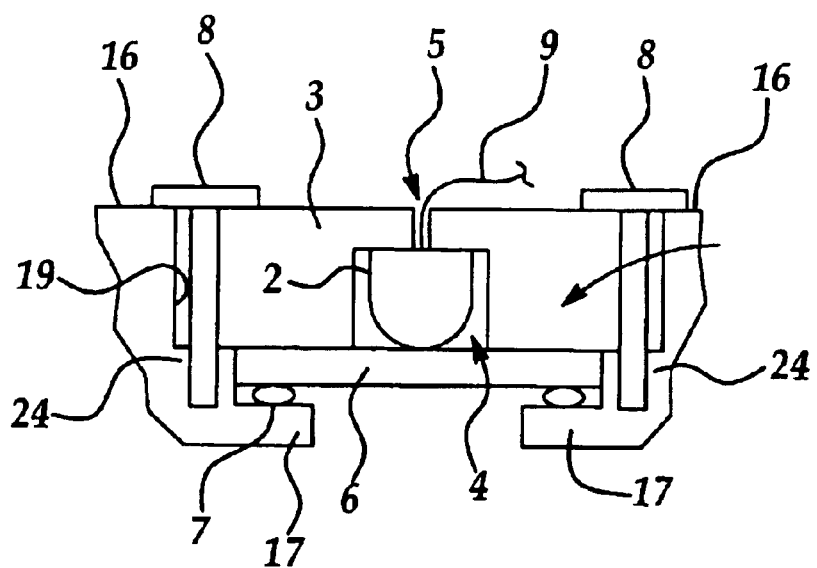
FIG. 4 is an enlarged sectional view, taken along section line 4 in FIG. 2, more particularly illustrating an illustrative structure for mounting each optical sensor in the lid of the plasma process chamber according to the present invention.

Referring next to FIGS. 2–4, a plasma process chamber according to the present invention is generally indicated by reference numeral 1 in FIG. 2. The lid 16 of the plasma process chamber 1 is fitted with multiple optical sensors 2 that are capable of monitoring the brightness or light reflection of the underlying gas distribution plate 18. As illustrated in FIG. 3, the multiple sensors 2 are typically distributed spatially in the lid 16 in such a manner that four sensors 2 are circumscribed by an imaginary outer circle 32 (illustrated in phantom) and four additional sensors 2 are circumscribed by an imaginary inner circle 33 (illustrated in phantom). However, it is understood that any desired number of the sensors 2 may be arranged in any desired pattern in the lid 16 sufficient to monitor selected areas or all areas of the underlying gas distribution plate 18.

Discrepancies or asymmetries in the relative brightness or opacity of the inner regions of the gas distribution plate 18 with respect to that of the outer or peripheral regions of the gas distribution plate 18 indicate the buildup of a material coating or accretion on one or more regions of the plate 18 exclusive of the other regions of the plate 18. Additionally, a sudden increase in the brightness or light reflective index of one region with respect to the relative opacity of the other regions of the disc may indicate dislodging of a potentially contaminating portion or portions of the coating from the plate 18. This data is sent through sensor wiring 9 to a conventional process controller 30, which is connected to the control system of the plasma process chamber 1. The process controller 30 is programmed according to the knowledge of those skilled in the art to calculate light reflective indices using the incoming data input from the respective optical sensors 2; and detect any differences in light reflective indices among the multiple optical sensors 2 which may reflect the differences in brightness or opacity between those areas of the gas distribution plate 18. In the event that there are significant differences (about 10% or more) between the reflective indices calculated using the data input from the respective optical sensors 2, the process controller 30 terminates operation of the control system to prevent initial or further contamination of the semiconductor wafer 20. Alternatively, the process controller 30 may be programmed to compare the brightness or opacity of the gas distribution plate 2 with a known standard for the brightness or opacity of the gas distribution plate 2, in which case the process controller 30 terminates operation of the control system when the light reflective index or brightness of the gas distribution plate 2 deviates from the control value by at least about 1, and typically, about 10%.

As further illustrated in FIG. 2, in another embodiment, the optical sensors 2 can be wired to an alarm 31, which can be an audio alarm, a visual alarm, or both, according to the knowledge of those skilled in the art. The discrepancy or asymmetry in brightness between the various regions of the gas distribution plate 18 or sudden change in the light reflective index between the areas of the plate 18 or with respect to a standard value is thus relayed to the alarm 31, which alerts to operating personnel audibly or visually, of a material coating buildup or accretion on or dislodging of a contaminant portion of the material coating from the gas distribution plate 18. In that event, operating personnel have sufficient warning to manually terminate operation of the plasma process chamber 1 before initial or additional particulate contamination to the wafer 20 occurs. The contaminated gas distribution plate 20 can then be cleaned to prevent further contamination of wafers 20 in the chamber interior 13. In still another embodiment, the alarm 31 may be incorporated in the circuitry of the process controller 30 according to the knowledge of those skilled in the art, such that operation of the plasma process chamber 1 is terminated while the alarm 31 alerts operating personnel to the presence of material accretion on or dislodging from the gas distribution plate 18.

FIG. 4 illustrates a representative structure for mounting each optical sensor 2 in the lid 16 of the plasma process chamber 1. Each sensor 2 is contained in a sensor cavity 4 provided in a sensor retainer disc 3, and each sensor retainer disc 3 is seated in a sensor opening 19 in the lid 16 and rests on a retainer disc shoulder 24 of the lid 16. Fasteners 8 typically extend through registering openings (not illustrated) provided in the sensor retainer disc 3 and retainer disc shoulder 24, respectively, to secure each sensor retainer disc 3 in the corresponding sensor opening 19. A quartz sensor lens 6 and an o-ring 7 are interposed between the bottom surface of the sensor retainer disc 3 and an annular flange 17 in the lid 16, and the sensor lens 6 closes the bottom of the sensor cavity 4. Sensor wiring 9, which extends from the optical sensor 2 and is connected to the process controller 30, passes through a wiring opening 5 provided in the upper portion of the sensor retainer disc 3. While the foregoing describes a representative structure for mounting each sensor 2 in the lid 16, it will be appreciated by those skilled in the art that other mounting structures are possible without departing from the spirit and scope of the invention.

While the preferred embodiments of the invention have been described above, it will be recognized and understood that various modifications can be made in the invention and the appended claims are intended to cover all such modifications which may fall within the spirit and scope of the invention.

What is claimed is:

1. An apparatus for detecting material accretion and peeling in a system, comprising:
    a plasma process chamber having a chamber interior for containing processing operations and comprising a gas distribution plate in said chamber interior;
    a plurality of optical sensors provided in said plasma process chamber in light receiving relationship with respect to light reflected from said gas distribution plate for monitoring relative brightness between various regions of said gas distribution plate; and
    an alarm operably connected to said plurality of optical sensors for activation by said plurality of optical sensors when said relative brightness varies by at least about 1%.

2. The apparatus of claim 1 further comprising a lid provided on said chamber and wherein said plurality of optical sensors are provided in said lid.

3. The apparatus of claim 1 wherein said relative brightness varies by about 3%–10%.

4. An apparatus for detecting material accretion and peeling in a system, comprising:
    a chamber having a chamber interior for containing processing operations and comprising a surface in said chamber interior; said chamber comprises a plasma process chamber and said surface comprises a gas distribution plate;
    a process controller operably connected to said chamber for terminating said processing operations in said chamber interior; and
    a plurality of optical sensors provided in said chamber, said plurality of optical sensors arranged in at least two generally concentric circles and operably connected to said process controller for monitoring relative brightness between various regions of said surface and activating said process controller when said relative brightness varies by at least about 1%.

5. The apparatus of claim 4 further comprising a lid provided on said chamber and wherein said plurality of optical sensors are provided in said lid.

6. The apparatus of claim 4 further comprising an alarm operably connected to said plurality of optical sensors for activation by said plurality of optical sensors when said relative brightness varies.

7. The apparatus of claim 4 wherein said relative brightness varies by about 3%–10%.

8. The apparatus of claim 4 further comprising a lid provided on said chamber and wherein said plurality of optical sensors are provided in said lid.

9. The apparatus of claim 4 further comprising an alarm operably connected to said plurality of optical sensors for activation by said plurality of optical sensors when said relative briqhtness varies.

10. The apparatus of claim 4 wherein said relative brightness varies by about 3%–10%.

11. A method for detecting material accretion and peeling in a system, comprising the steps of:
    providing a plasma process chamber having a chamber interior for containing processing operations and comprising a gas distribution plate in said chanter interior;
    providing a plurality of optical sensors in at least two generally concentric circles in said chamber for monitoring relative brightness between various regions of said gas distribution plate;
    operably connecting a process controller to said chamber and said plurality of optical sensors;
    reflecting light from said gas distribution plate to said plurality of optical sensors; and
    transmitting a signal from said plurality of optical sensors to said process controller when said relative brightness varies by at least about 1% to terminate said processing operations.

12. The method of claim 11 further comprising providing a lid on said chamber and wherein said plurality of optical sensors are provided in said lid.

13. The method of claim 11 further comprising operably connecting an alarm to said chamber and transmitting a signal from said plurality of optical sensors to said alarm when said relative brightness varies.

14. The method of claim 11 wherein said relative brightness varies by about 3%–10%.

* * * * *